United States Patent [19]

Baker

[11] Patent Number: 4,996,658

[45] Date of Patent: Feb. 26, 1991

[54] SELF-CALIBRATING GLASS CONTAINER INSPECTION MACHINE

[75] Inventor: Russ J. Baker, Horseheads, N.Y.

[73] Assignee: Emhart Industries, Inc., Towson, Md.

[21] Appl. No.: 401,105

[22] Filed: Aug. 31, 1989

[51] Int. Cl.$^5$ .................... G01R 35/00; G06G 15/46; B07C 5/00

[52] U.S. Cl. .............................. 364/571.04; 364/473; 364/563; 209/522; 324/671

[58] Field of Search ...................... 364/571.01, 571.04, 364/473, 550, 551.01, 552, 563, 138; 209/522–524; 324/671, 699, 664, 686; 73/1 R

[56] References Cited

U.S. PATENT DOCUMENTS

| | | | |
|---|---|---|---|
| 3,936,665 | 2/1976 | Donoghue | 364/563 X |
| 4,109,511 | 8/1978 | Powers, Jr. et al. | 364/554 X |
| 4,208,625 | 6/1980 | Piso | 324/671 |
| 4,413,738 | 11/1983 | Pemberton et al. | 364/473 X |
| 4,457,772 | 7/1984 | Haynes et al. | 364/138 X |
| 4,476,533 | 10/1984 | Daudt et al. | 364/473 |
| 4,633,420 | 12/1986 | Masanobu | 364/563 |
| 4,639,263 | 1/1987 | Kulikauskas | 364/473 X |
| 4,691,830 | 9/1987 | Ahl et al. | 364/473 X |
| 4,694,158 | 9/1987 | Leser | 209/524 X |
| 4,799,177 | 1/1989 | Sarr | 364/563 |
| 4,860,229 | 8/1989 | Abbe et al. | 364/563 |

Primary Examiner—Joseph L. Dixon
Attorney, Agent, or Firm—Spencer T. Smith

[57] ABSTRACT

A glass container inspection machine including a bottle handling mechanism which presents glass containers to a capacitive sensor which provides a voltage signal representative of the thickness of the glass container, a computer which receives the voltage signals, a keyboard for inputting data into the computer, and a display. The thickness of a glass container is measured at four points, and as each point is presented to the sensor, the measured thickness in input into the computer, which stores the sensed voltages, correlates them to the input thicknesses, and calculates a curve used to determine glass thickness from sensed voltage. Alternatively, the minimum and maximum thicknesses of a glass container are measured, input into the computer, the container is passed through the machine, and the computer correlates the lowest and highest voltages sensed with the minimum and maximum thicknesses respectively, and uses this data to generate the calibration curve. The measured data is input by aligning a cursor with a data category on the display screen and entering the data via the keyboard. The computer senses the voltage(s) on the next bottle presented to the sensor and displays them on the screen in the selected data category.

3 Claims, 8 Drawing Sheets

```
ZERO              CALIBRATE         AUTO
HEAD              HEAD              CALIBRATE

CALIBRATION

CHANNEL 1         CHANNEL 2         CHANNEL 3         CHANNEL 4

THIK VOLT         THIK VOLT         THIK VOLT         THIK VOLT
.056 2.56         .056 2.32         .070 2.52         .070 2.30
.098 3.20         .098 2.74         .120 3.26         .120 2.84
.058 2.68         .058 2.38         .075 2.78         .075 2.36
.092 3.16         .092 2.72         .097 3.20         .097 2.76

10:57             10:57             10:57             10:57
 19-APR-89         19-APR-89         19-APR-89         19-APR-89
     OK                OK                OK                OK

AFTER ZEROING, PLACE STANDARD THICKNESS
         SAMPLE IN READ POSITION AND ENTER
        THICKNESS FOR DESIRED POINTS. ENTER 0
                   TO REMOVE POINT

LINE #1   10:57   19-APR-89
```

FIG. 7

```
              CALIBRATE         AUTO
              HEAD              CALIBRATE

CHAN 1:  THIK VOLT     CHAN 2:  THIK VOLT
              STD1 MIN                STD1 MIN
                   MAX                     MAX
              STD2 MIN                STD2 MIN
                   MAX                     MAX
              10:57  19-APR OK       10:57  19-APR OK

CHAN 3:  THIK VOLT     CHAN 4:  THIK VOLT
              STD1 MIN                STD1 MIN
                   MAX                     MAX
              STD2 MIN                STD2 MIN
                   MAX                     MAX
              10:57  19-APR OK       10:57  19-APR OK

AFTER ZEROING, ENTER DESIRED MIN
              AND / OR MAX THICKNESS, RUN STD
                       THROUGH MACHINE

LINE #1   10:57   19-APR-89
```

FIG. 8

SELF-CALIBRATING GLASS CONTAINER INSPECTION MACHINE

FIELD OF THE INVENTION

The invention in general relates to machines for inspecting glass containers, and more particularly to such a machine that is self-calibrating.

DESCRIPTION OF THE PRIOR ART

It is important to inspect glass containers frequently during and after manufacturing to discover problems in the manufacturing process and to discard containers that are defective. For example, inspections are made for flaws such as checks, cracks, chips and line overs as described in U.S. Pat. No. 4,488,684 issued to Mark P. Claypool, sidewall defects as described in U.S. Pat. No. 4,679,075 issued to Read Williams, et al, proper sealing of the finish on mouth of the container as described in U.S. Pat. No. 4,837,707 issued to Stephen M. Giometti, et al, and wall thickness detectors which generally operate by rolling the glass container along an elongated capacitive sensor which senses the capacitance and hence the wall thickness of the container and rejects those for which the wall thickness is below a set value. These inspection systems are generally set up or calibrated by placing a sample container in the inspection apparatus and manually adjusting various controls until the desired output is reached. Since glass container inspection machines are generally very sensitive, and glass containers vary significantly from type to type, the systems must be recalibrated each time a different size or style of container is to be inspected. Since the inspection lines do not operate during the calibration process, significant line down time occurs with such systems. For example in capacitance type wall thickness inspection systems, an oscillator is used to determine the capacitance of the container and generate a voltage which may be converted to data representative of the wall thickness. Such apparatus must be calibrated if the conversion of capacitance to voltage to dimensional data is to be accurate. In the prior art, such calibration has been done by first zeroing the sensor with no container present, placing a glass standard against the sensor, manually adjusting a calibration control until a meter reads the thickness marked on the standard, removing the standard and allowing the meter to return to zero, returning the glass standard into position against the sensor, adjusting a reject limit control, then rezeroing the system. This was all done manually. Since different sensor heads must be used for different container sizes and glass types and each head must be separately calibrated each time it is used, a significant amount of line down time is required for calibration. Moreover, the glass standards that are used in the prior art are relatively fragile so they cannot be handled by conventional machinery, therefore, they must be carefully aligned by hand during the calibration process.

SUMMARY OF THE INVENTION

It is an object of the invention to provide a glass container inspection machine which may be calibrated more quickly than prior art glass container inspection machines.

It is another object to provide the above object in a glass container inspection machine that can be calibrated with a simpler set of operator actions than the prior art systems.

It is still another object of the invention to provide a glass container inspection machine that can be calibrated by simply entering the values of the property inspected for a sample container into the machine, while permitting the machine to inspect the sample.

It is a further object of the invention to provide a glass container inspection machine which may be calibrated simply by entering selected values of a property of a sample container into the machine and then moving the sample container through the inspection machine.

It is still a further object of the invention to provide a glass container wall thickness inspection machine that provides one or more of the above objects.

It is yet another object of the invention to provide a glass container wall thickness inspection machine which provides the above object and may be calibrated by entering the minimum and maximum wall thickness of a container sample into the machine and running the sample through the machine.

It is another object of the invention to provide a glass container inspection machine that provides one or more of the above objects and automatically captures data and calculates a calibration curve.

The invention provides a glass container inspection machine comprising: sensing means for providing a sensed data signal representative of a property of a glass container presented to it; mechanical handling means for presenting at least a portion of a glass container to the sensing means; output means responsive to the sensed data signal for providing an output signal determined by the property; storage means for storing at least two pairs of data signals; input means for entering into the storage means an input data signal representing the property for a container sample; capture means communicating with the sensing means for storing a sensed data signal in the storage means and correlating it to a selected input data signal; and calibration means for utilizing the data signals stored in the storage means to calibrate the apparatus so that the output signal accurately reflects the measured property of the glass container. Preferably, the capture means comprises means for capturing the measured data signal being provided when the input means is activated and correlating it to the input data signal input by said activation. In another aspect, the capture means comprises means for capturing a sensed data signal from the next container presented to the sensing means after the input data signal is entered. Preferably, the calibration means comprises a means for generating a curve representing the property as a function of the sensed data signal. Preferably, the storage means is a digital computer and said input means is a keyboard.

Preferably, the property is the wall thickness of the glass container and the sensed data signal is a sensed thickness signal. Preferably, the capture means includes means for capturing the sensed thickness signal corresponding to the thinnest portion of a selected container and means for capturing the sensed thickness signal corresponding to the thickest portion of a selected container. Preferably, the input means comprises means for inputting the minimum and maximum thicknesses of the portion of the glass container presented to the sensing means, and the capture means comprises means responsive to the input means being activated for capturing the sensed thickness signals corresponding to the thinnest and thickest portion of the next container presented to the measuring means after the input means is activated. Preferably, the measured thickness signal is an electrical voltage signal and the capture means comprises means for capturing the lowest and highest voltage signals provided for a selected container. Preferably, the sensing means comprises means for providing a continuous voltage signal representative of the thickness of a glass container presented to the sensing means, and the capture means comprises: sampling means for sampling the voltage generated by the sensing means at a selected number of sample locations around the wall of the glass container; first means for determining the lowest of the sampled voltages; second means for determining the highest of the sampled voltages; and correlation means for correlating the lowest sampled voltage to the minimum thickness and the highest sampled voltage to the maximum thickness. Preferably, the sensing means comprises a plurality of sensing heads each having a corresponding data channel and the calibration means comprises means for generating a voltage versus thickness curve for each of the plurality of data channels. Preferably, the capture means comprises means for capturing the sensed data signal from a glass container being moved past the measuring means by the mechanical handling means at the normal operating speed of the glass container inspection machine.

The invention also provides, a method of calibrating a glass container inspection machine comprising the steps of: providing a glass container inspecting machine that provides an output representative of the minimum and maximum thickness of at least a selected portion of a glass container; measuring the minimum thickness of at least a selected portion of a selected glass container and the maximum thickness of at least a selected portion of a selected glass container; causing the machine to provide an output representative of the measured minimum and maximum thicknesses; and using the measured minimum and maximum thicknesses and the output representative of said measured minimum and maximum thicknesses to calibrate the machine. Preferably, the output comprises a voltage and the step of using comprises generating a voltage versus thickness curve.

The invention not only provides an apparatus and method of calibrating a glass container inspection machine that is faster and simpler than the calibration apparatus and methods of the prior art, but also permits the use of ordinary glass containers as standards. Numerous other features, objects and advantages of the invention will become apparent from the following detailed description when read in conjunction with the accompanying drawings.

BRIEF DESCRIPTION OF THE DRAWINGS

In the drawings;

FIG. 7 shows the display screen when the embodiment employing the container measurements of FIG. 5 is selected using the machine of FIG. 1;

FIG. 7 shows the display screen when the embodiment employing the container measurements of FIG. 6 is selected using the machine of FIG. 1;

DESCRIPTION OF THE PREFERRED EMBODIMENT

Figure 1:
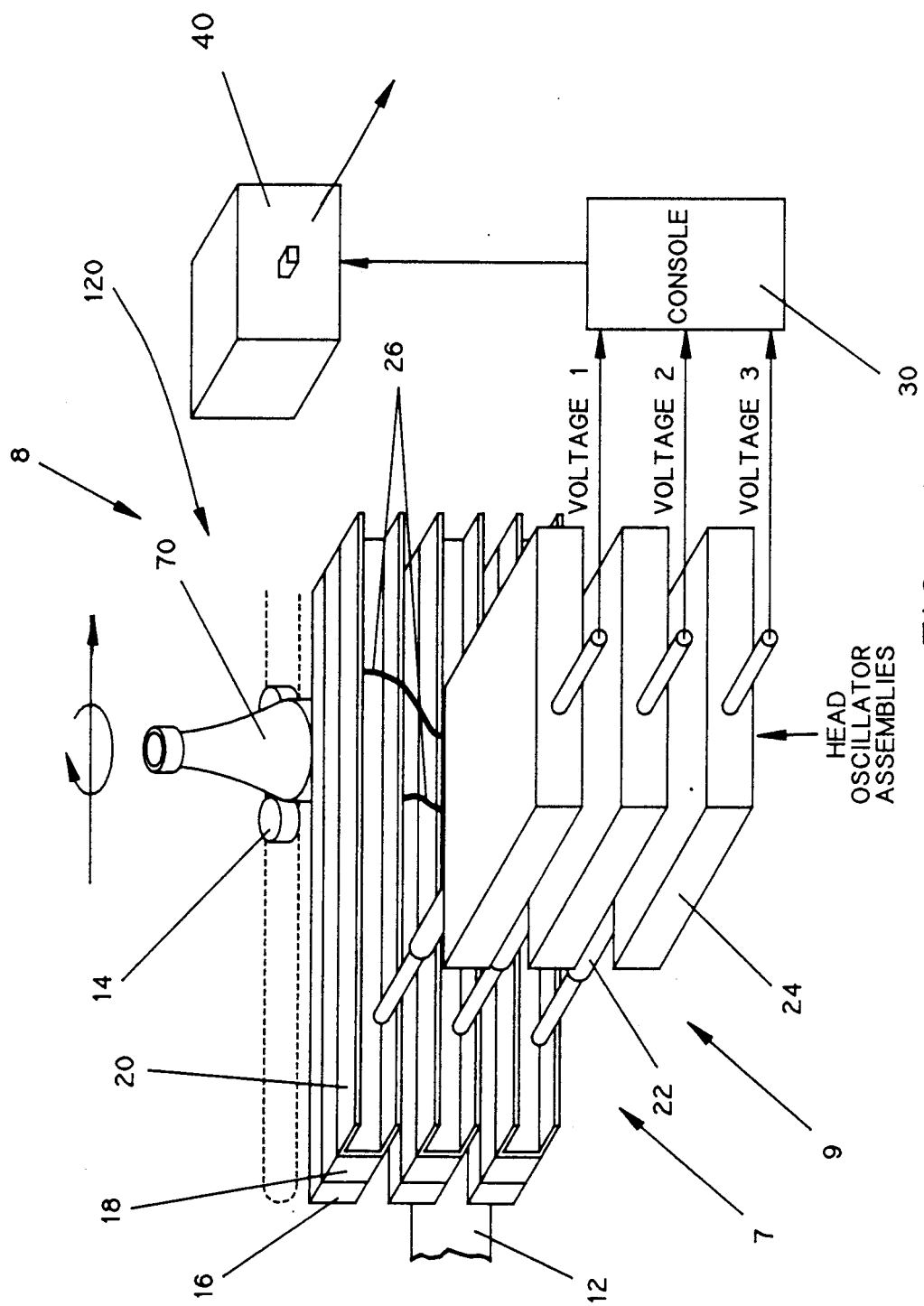
FIG. 1 is a front diagramatic perspective view illustrating the principal components of the preferred embodiment of a glass container inspection machine according to the invention.
Figure 2:
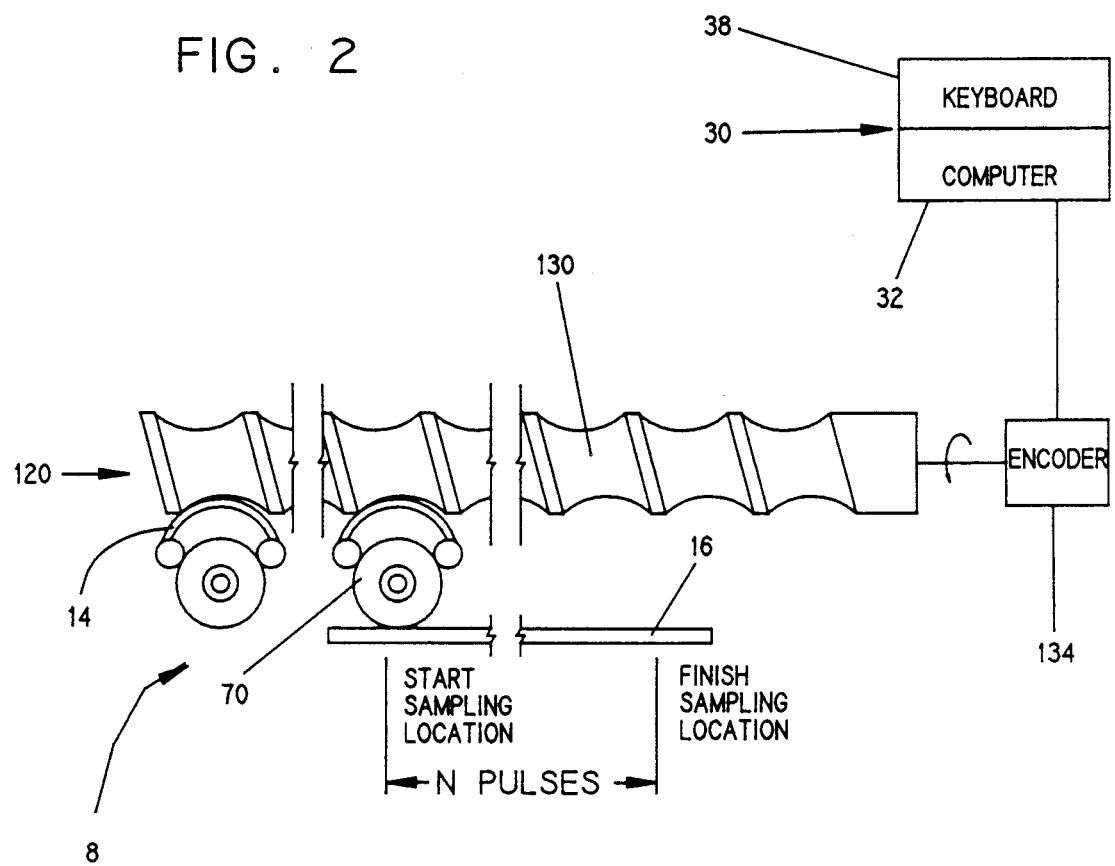
FIG. 2 is a top diagramatic view illustrating the container handling and voltage sampling apparatus of the machine of FIG. 1.
Figure 3:
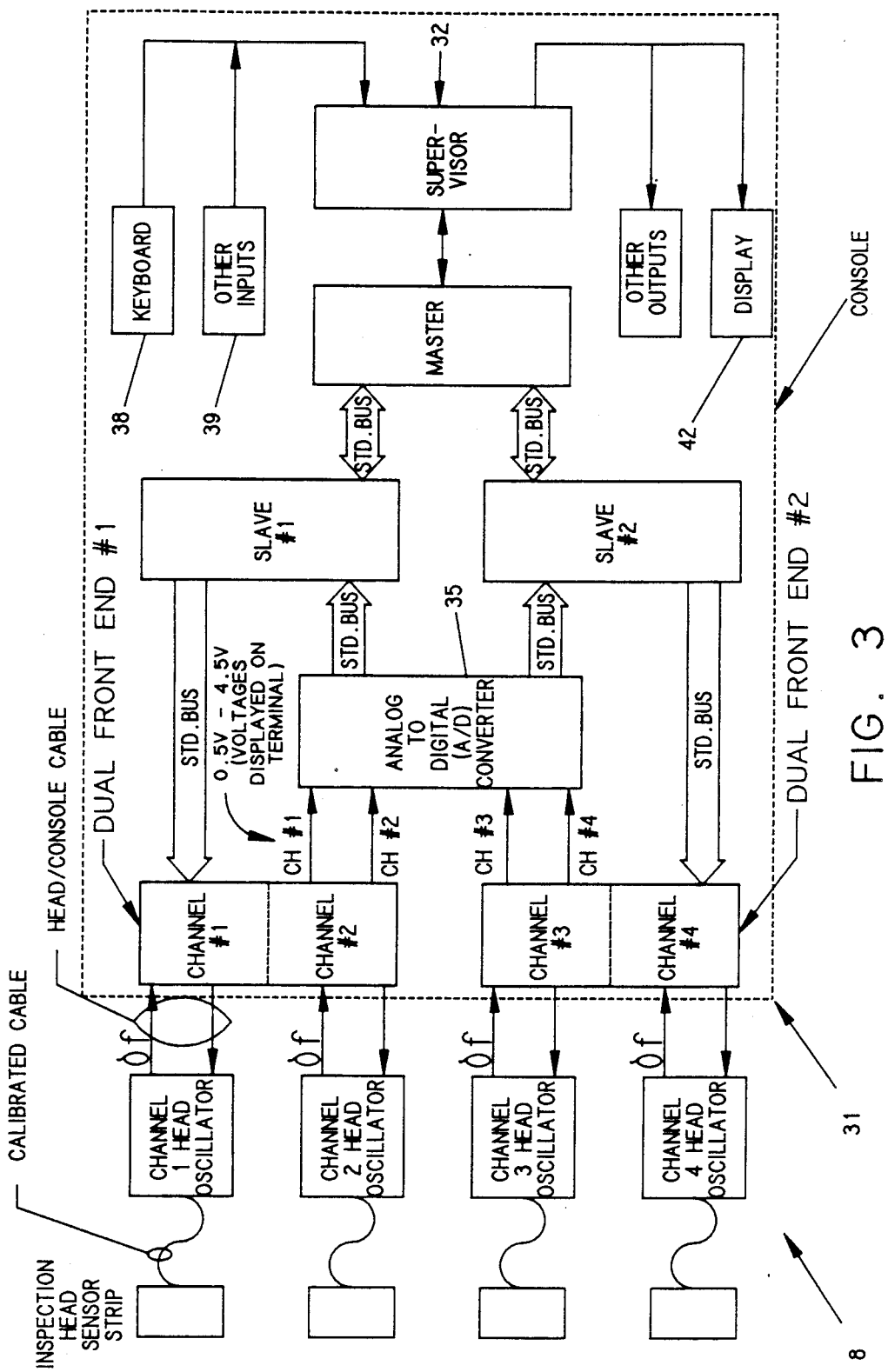
FIG. 3 is a block diagramatic view of the electronics of the glass container inspection machine of FIG. 1.

Directing attention to FIG. 1, a portion of a test station 7 of a glass container inspection machine 8 according to the invention is shown. For simplicity, only three sensing head assemblies 9 are shown although the complete preferred embodiment would have four (see FIG. 3). It is understood that the particular embodiment shown is intended to be exemplary, is shown for purposes of illustration only, and is not intended to limit the invention to the particular embodiment. The glass container inspection machine 8 has a station 7 for testing a container 70, which in the preferred embodiment is a round bottle, which is advanced through the test station 7 by mechanical handling means 120, which comprises a support plate 12 and a bottle carrier 14. During its displacement past the test station, the carrier 14 forces the bottle against a number (three shown) of parallel, horizontally extending and vertically spaced capacitance sensing strips 16 which are secured to resilient foam strips 18 mounted on suitable brackets 20. The brackets are connected by posts 22 to corresponding housings 24 for oscillator assemblies 9 which receive a capacitance signal via calibrated cables 26 and generate voltage signals representative of the wall thickness of bottle 70, which signals are supplied to the console 30, which includes front end electronics 31 and computer 32 (FIG. 3). FIG. 2 presents a top view of the inspection machine 8 which further illustrates the handling means 120 which advances the bottle 70 to and through the test station. Handling means 120 includes an elongated cam 130 which rotates at a constant speed. The cam 130 engages the carrier 14 at a position prior to the sensing strip 16. The cam 130 advances the carrier 14 to the right thereby translating a captured bottle 70 to the right. The rotational position of the cam 130 is monitored by an encoder 134 which provides electrical pulses corresponding to positions of the cam and thus positions of the bottle 70. After sensor 16 detects the presence of the bottle, it waits a certain number of pulses (based on the size of the sensor 16) to guarantee that the bottle is completely in front of the sensor. This determines the starting position. A counter within computer 32 is set to zero. The computer 32 then samples the voltages on each of the four channels (FIG. 3) at each subsequent count of encoder 134 until the count reaches a selected number (N) which corresponds to a Finish Sampling Location which assures that the entire periphery of the bottle has been sampled. For smaller bottles, a portion of this peripheral ring will be analyzed twice. The operator inputs the sensor size via keyboard 38 or other data input means 39 and the computer 32 sets the correct N number for the maximum size container that can be tested on that sensor. Data samples are taken around the bottle at each sensor and then evaluated to identify the lowest and highest voltage around the bottle. These voltages are stored in suitable registers in computer 32 which are updated whenever a lower or higher voltage is sensed until readings have been taken completely around the bottle. A highest voltage and lowest voltage register can be provided for each sensor (channel). These voltages are representative minimum and maximum wall thickness of the bottle 70 and are converted to wall thickness by the computer 32 using a curve of wall thickness as a function of voltage. A more detailed description of the capacitive sensing system of FIGS. 1 and 3 is given in U.S. patent application Ser. No. 414,920 and a more detailed description of the voltage sampling apparatus and method is given in U.S. Pat. No. 4,862,062, which patents are hereby incorporated by reference. The machine 8 is calibrated by inputting at least two wall thicknesses from a sample container into the computer 32 via keyboard 38 and then presenting the measured container to the sensor strips 16. The computer then automatically senses the voltage corresponding to the sample presented and uses the input thicknesses and the sensed voltages to generate the thickness as a function of voltage curve mentioned above to calibrate the machine. Two preferred embodiments of the machine and method of the invention will be described. The first shall be referred to as the "standard calibration mode" and the second as the "auto calibration mode".

Figure 4:
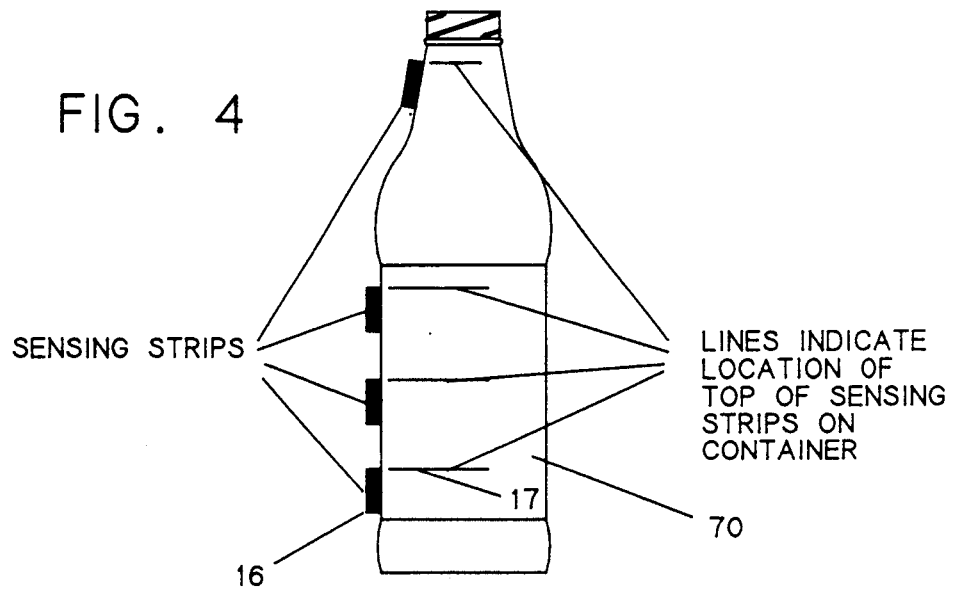
FIG. 4 shows typical locations of inspection heads on a glass container.
Figure 5:
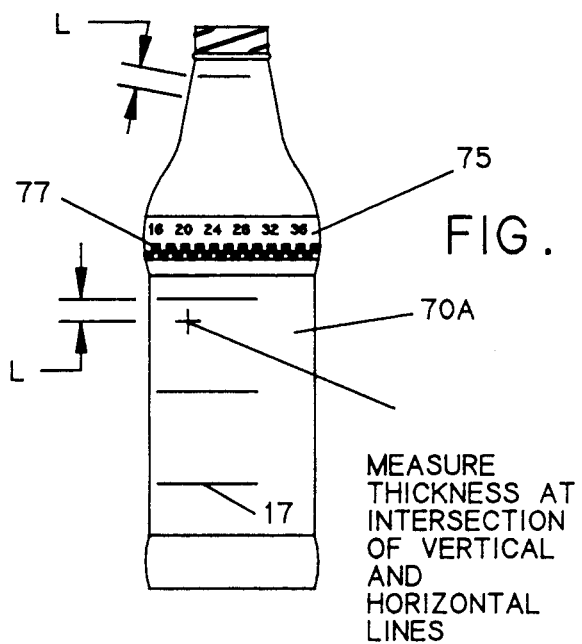
FIG. 5 shows locations for measuring bottle thickness according to one preferred method of the invention.

The standard calibration mode shall be described in conjunction with FIGS. 1 through 4, and FIGS. 5, 7, and 9. FIG. 4 illustrates how the sensing strips 16 are placed against the container 70 in the preferred embodiments. Four lines, such as 17, indicate the location of the top of the sensing strips on the container, which lines shall be of assistance in discussing FIGS. 5 and 6. At some time prior to operating the machine in the standard calibration mode, the container 70A is prepared as shown in FIG. 5. A reference strip 75 is attached to the container 70A at a location which will not interfere with the sensing strips 16. N reference positions are marked on the reference strip 75. The bottle thickness is measured at a number of positions around the bottle circumference, each of which positions are determined by the intersection of a vertical line passing through one of the reference positions on the reference strip 75 and a horizontal line a distance L below each of the lines 17. The distance L is preferably half the width of sensing strip 16. Preferably, the bottle thickness is measured at at least four positions for each sensing strip. The measurements are made in any conventional manner, such as with a Kraut Kramer Branson ultrasonic pulse-echo, thickness gauge or a mechanical measuring device. For ease of future use of the bottle as a standard, the thickness may be measured at each of the reference positions, which will allow any of the reference positions to be used to calibrate the machine. Each of the measured thicknesses represents a container thickness sample. These thickness samples only need to be prepared once and can be reused anytime the machine needs to be calibrated.

If the machine has not been previously been set up, or if a component has been changed since it was set up, it may need to be zeroed prior to calibration. The machine is zeroed by using keyboard 38 to enter the "Zero Head" mode. In Zero Head mode, a screw which adjusts a variable capacitor in the measuring oscillator (see U.S. Pat. No. 4258-18 CIP) is turned until the output stabilizes, which is an indication that the phase-locked loop has locked. It is then turned further until the voltage is set at the desired "zero" voltage which in the preferred embodiment is 0.48 volts. It is then turned further until a bar graph on the zero head screen disappears, which sets the temperature compensating automatic zeroing circuit to the midpoint of its range, which in the preferred embodiment is 7.5 volts. Once the machine has been zeroed, it generally will remain zeroed until a component, such as a sensing strip or head oscillator, is changed.

Figure 9:
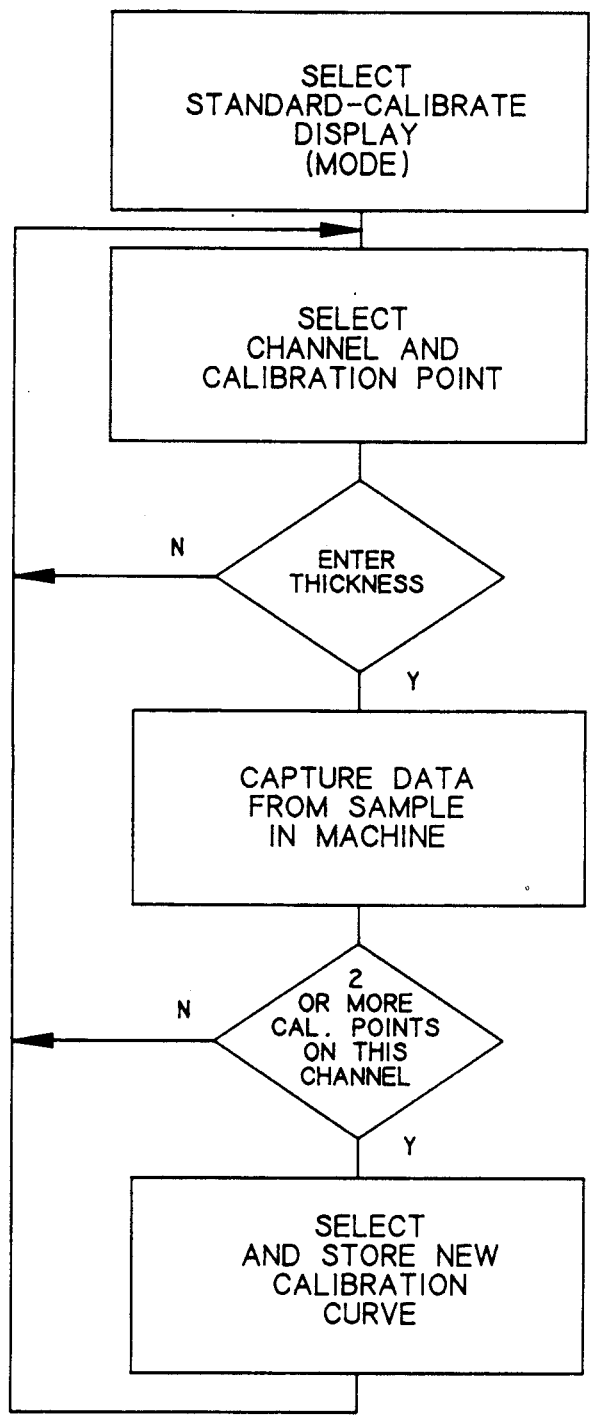
FIG. 9 shows a flow chart of the preferred method and apparatus using the container measurements of FIG. 5, the screen of FIG. 7, and the machine of FIG. 1.

If the machine is zeroed, it may then be calibrated. A flow chart showing how the software in computer 32 leads the operator through the standard calibration procedure and calibrates the machine is shown in FIG. 9. The standard calibration mode is selected using keyboard 38. This brings up the "Calibrate Head" screen on display 42, a typical example of which is shown in FIG. 7. A lighted area appears behind the "Calibrate Head" heading to indicate the display is in the Calibrate Head mode. The desired channel and calibration point are then selected by moving a lighted cursor to one of the sixteen numerical positions on the screen by using conventional cursor keys on keyboard 38. If the container 70A which has been measured is not yet in position to be sensed by the machine, it should now be placed in a carrier 14 and advanced to the center of the sensing area of the strips 16. The bottle 70A may then be rotated by hand between the carrier 14 and the sensing strips until a desired container thickness sample indicated by a selected reference position marked on the strip 75 is against the sensing strip 16 corresponding to the selected channel. The manually measured thickness for that particular container sample is then entered into the computer 32 via keyboard 38. When the "enter" key is pressed to input the thickness data, the machine displays the thickness entered in the "thik" column at the cursor and captures the voltage output on the selected channel by reading it, storing it in computer 32, and displaying it on the screen in the "volt" column at the cursor. The software then directs the computer to check on whether two or more calibration points have been entered on the selected channel, that is, whether data from two or more container samples have been captured. If not, the software returns to the "Select Channel and Calibration Point" operation. The container 70A is then manually turned to a new container sample, i.e. a new reference position, and the cursor is moved to a new screen position, and the thickness corresponding to that position is entered and the voltage is captured, i.e. read, stored, and displayed as before. When two or more calibration points have been captured, the software directs the computer to calculate a calibration curve, using the function:

$$V(T) = A \times T/(1 + B \times T)$$

where V is the voltage, T is the wall thickness, A is the coefficient describing the relationship between thickness and voltage for small wall thicknesses, and B is the coefficient describing the relationship between voltage and wall thickness for large thicknesses. Preferably, "pseudo" linear regression techniques are used to calculate A and B from the stored pairs of V and T. After calculating the calibration curve, the software returns the system to the "Select Channel and Calibration Point" operation. Data for up to four container samples, i.e. four points on one or more containers, may be captured for each channel, and after each capture of data, the system calculates a new calibration curve. All four pairs of data points should be captured for greatest accuracy. Preferably, one point should be chosen close to the maximum thickness measurable (3.8 mm in the preferred embodiment), one point is chosen near the minimum measurable wall thickness (the minimum wall thickness that is mechanically handleable by wall thickness inspecting machines in the preferred embodiment), and two points in between. If a single point shows bad calibration, for example a thickness of 0.058 has a lower voltage than a thickness of 0.050, that point can be individually reentered and recaptured. A point may be removed from the calibration procedure by entering a thickness of zero.

Figure 6:
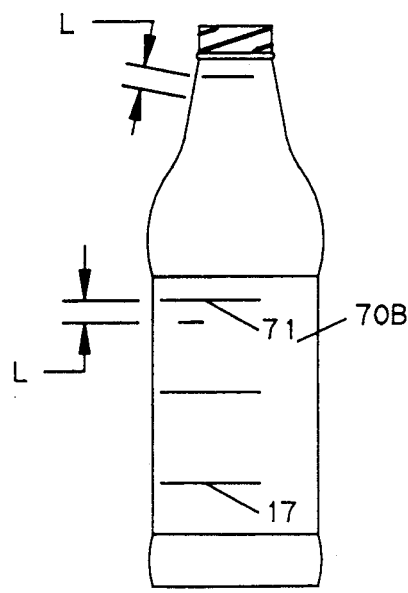
FIG. 6 shows the locations for measuring bottle thickness according to an alternative preferred method of the invention.

Using the above standard calibration apparatus and method, the machine may be calibrated accurately and reliably in just a few minutes. The invention also provides an automatic calibration apparatus and method which is even faster. This automatic calibration apparatus and method will now be described in reference to FIGS. 1 through 4, 6, 8, 10A and 10B. Referring to FIG. 6, for this apparatus and method a sample is prepared by determining the minimum and maximum thicknesses at a distance L below the lines 17 indicating the location of the top of the sensing strip for each of the four sensing strips 16. For example, the thickness would be measured around the circumference of the container 70B at the height shown by the line 71 in the figure. The minimum and maximum thicknesses are recorded. Each of these measured minimum thicknesses and each of the measured maximum thicknesses represent a container thickness sample. Preferably, two bottles 70B are measured, one having a maximum thickness that is near the maximum measurable and the other having a minimum thickness near the minimum measurable are chosen.

Figure 10A:
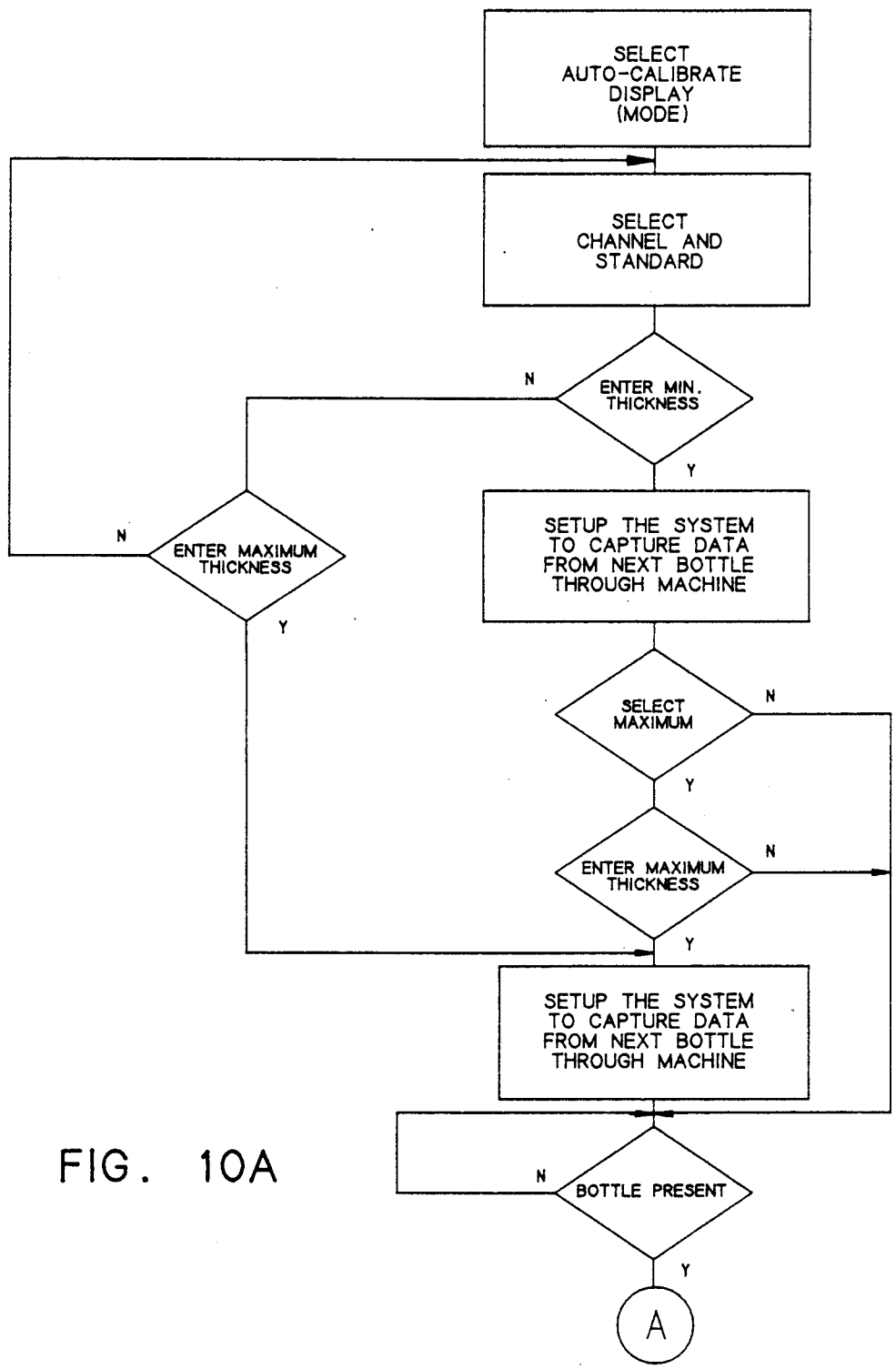
FIGS. 10A and 10B show a flow chart of the preferred method and apparatus using the container measurements of FIG. 6, the screen of FIG. 8, and the machine of FIG. 1.
Figure 10B:
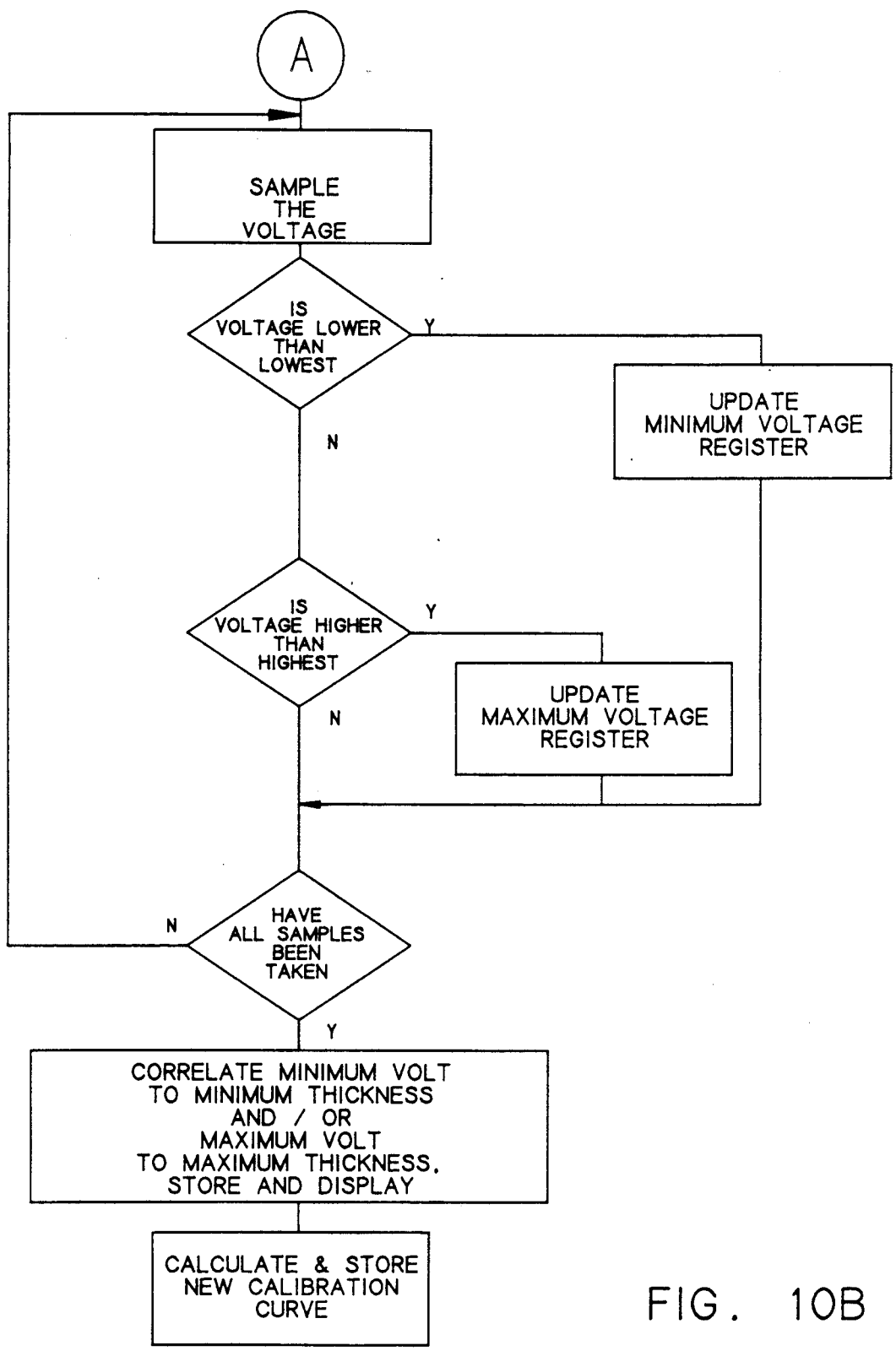

If the machine has not been zeroed, it should be zeroed as discussed above. The auto-calibrate mode is selected via the keyboard 38 and a screen as shown in FIG. 8 is displayed with the "auto calibrate" heading highlighted. A flow chart showing how the software in computer 32 leads the operator through the auto-calibrate procedure and calibrates the machine is shown in FIGS. 10A and 10B. The letter A in the circle indicates the point where the flow chart of FIG. 10A flows into the flow chart of FIG. 10B. The software is designed so that when the auto-calibrate mode is entered the operator must first select the STD1 MIN position. If a number representing the thickness is entered, the software sets up the system to capture the data from the next bottle through the machine. The operator may then either move the cursor down to select a maximum thickness or send a bottle through the machine, which alternative is represented by the "N" branch of the "Select Max." decision box. If the cursor is moved to the Max position for the same channel and standard, the maximum may be entered and the system is again readied to capture data from the next bottle through the machine. Alternatively, the cursor may immediately be moved to the Max position without entering a minimum thickness, which alternative is indicated by the "N" branch of the "Enter Min. Thickness" decision box. If the maximum is entered at this point, the system is set up to capture data from the next bottle through the machine. If the cursor is moved to another channel or standard without running a bottle through the machine, which alternative is represented by the "N" branch of the "Enter Max. Thickness" decision box at the extreme left in FIG. 10A, then the software causes the system to revert to the previous settings for the channel and standard exited. In this way, the cursor may be moved through the various channels and standards without entering thickness data or running a bottle through, until the desired channel and standard is reached. Then a minimum thickness, a maximum thickness, or both are input into the computer and a bottle is sent through the machine. When a bottle is detected, the software enters the flow chart shown in FIG. 10B. This flow chart, except for the last process box (Calculate and Store New Calibration Curve) represents the operations performed by the machine to capture the data signals, i.e. voltage signals, corresponding to the container samples for which the minimum and/or maximum thickness data was entered. As described above in reference to FIG. 2, as one of the bottles 70B is being rolled across the sensor strips 16, the software causes the system to take N samples of the voltage at positions determined by the pulses from encoder 134. Each time a voltage sample is taken, the computer compares it to the voltage stored in the minimum voltage register, and if it is lower, updates the register, then compares the voltage to the voltage in the maximum voltage register, and if it is higher, updates the maximum voltage register. The software then looks to see if all samples have been taken, and if not, takes another sample and repeats the steps. When all samples have been taken, the voltage in the minimum voltage register is stored and displayed on the screen as the voltage corresponding to the minimum thickness that was input, the voltage in the maximum voltage register is stored and displayed on the screen as the voltage corresponding to the maximum thickness that was input, and then a calibration curve is calculated as discussed above using these and any previously existing calibration points from previous standard bottles that were run through the machine. Preferably, two bottles are run through the machine, one having a minimum which is close to the minimum detectable thickness and one having a maximum that is close to the maximum detectable thickness. Such a selected pair of bottles will provide a spread of calibration points that will result in an accurate calibration curve. Again, if a single point is showing bad calibration, that point can be individually reentered by entering just the one data point before running a standard bottle.

After either calibration mode, but particularly after the auto-calibrate mode, one may fine-tune the calibration to account for any difference between the method or tools used to initially measure the container samples and the above-described wall thickness inspection system. To do this, run the machine for a while and collect a rejected sample. Then measure the appropriate property (minimum or maximum thickness or whatever property the reject was based on). If the measured values are too high or too low, run the calibration sample again and add or subtract one or two mil at a time until the machine is rejecting exactly as desired. The final values for thickness used should be recorded and used for the container samples in future calibrations. This fine-tuning needs to be done only once for any sample.

Once the calibration curve is calculated, it is used to provide output thickness signals based on the sensed voltage. The same procedure and apparatus may be used to provide calibration curves of capacitance versus thickness, or any other set of sensed and measured parameters. The output thickness signals may be used to operate a rejection mechanism 40 as discussed briefly above and more fully described in U.S. Patent No. 4,862,062.

It is a feature of the invention that in the auto-calibrate mode, the bottles are passed through the machine by the normal bottle handling mechanism at the normal rate of speed at which the machine inspects bottles. Further, ordinary bottles are used for the calibration standards. Once the bottles are selected and measured, they may be used to quickly calibrate the machine after changeover is made to a new type of bottle, or whenever some component is replaced.

A novel apparatus and method for calibrating a glass container inspection machine has been described. It is evident that those skilled in the art may now make numerous uses and modifications of and departures from the specific embodiments described herein without departing from the inventive concepts. For example, the concepts of the invention can be applied to other container inspection systems. Other means for capturing the required data points as a bottle is being passed through the machine may be substituted. Other mathematical techniques and equations may be used to generate a calibration curve. Many other variations may be described. Consequently, the invention is to be construed as embracing each and every novel feature and novel combination of features present in and/or possessed by the container inspection apparatus described.

What is claimed is:

1. A glass container inspection machine comprising
   sensing means for providing a voltage signal representative of the thickness of the wall of a glass container,
   means for presenting a glass container to said sensing means,
   means for storing at least two voltage signals provided by said sensing means representative of the thickness of the wall of the glass container at at least two selected locations,
   means for inputting the actual thickness of the wall of the sensed container corresponding to each of said at least two selected locations, and
   calibration means for equating said at least two voltage signals with said inputted corresponding actual thicknesses and for generating a curve representing actual thickness as a function of sensed voltage.

2. A glass container inspection machine according to claim 1, wherein two of said selected voltage signals correspond to be sensed.

3. A glass container inspection machine according to claim 2, wherein said storing means comprises means for storing voltage signals corresponding to the maximum and minimum wall thicknesses of two glass containers.

* * * * *